(12) United States Patent
McColl et al.

(10) Patent No.: US 10,506,994 B2
(45) Date of Patent: Dec. 17, 2019

(54) APPARATUS FOR A RADIOGRAPHIC DEVICE

(71) Applicant: GENERAL ELECTRIC COMPANY, Schenectady, NY (US)

(72) Inventors: Connor Douglas McColl, Oconomowoc, WI (US); Kevin Lee, Milwaukee, WI (US); Nicholas Konkle, Sussex, WI (US); Kevin Kinsey, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 207 days.

(21) Appl. No.: 15/689,096

(22) Filed: Aug. 29, 2017

(65) Prior Publication Data

US 2019/0059836 A1  Feb. 28, 2019

(51) Int. Cl.
*A61B 6/00* (2006.01)
*G01T 7/00* (2006.01)

(52) U.S. Cl.
CPC .............. *A61B 6/4283* (2013.01); *G01T 7/00* (2013.01)

(58) Field of Classification Search
CPC ... A61B 6/4233; A61B 6/4283; A61B 6/4405; B21D 51/52; G01T 1/244; G01T 7/00; G03B 42/04; H01L 27/14618; H01L 27/14634; H01L 27/14658; H01L 27/14676

See application file for complete search history.

(56) References Cited

U.S. PATENT DOCUMENTS

| | | |
|---|---|---|
| 5,804,832 A | 9/1998 | Crowell et al. |
| 6,897,449 B1 | 5/2005 | Hata |
| 7,189,972 B2 | 3/2007 | Ertel et al. |
| 7,488,946 B2 | 2/2009 | Hennessy et al. |
| 7,495,226 B2 | 2/2009 | Jadrich et al. |
| 7,569,831 B2 | 8/2009 | Jadrich et al. |
| 7,582,877 B2 | 9/2009 | Dobrusskin et al. |
| 7,745,797 B1 | 6/2010 | Liu et al. |
| 7,800,065 B2 | 9/2010 | Konkle et al. |
| 7,881,435 B2 | 2/2011 | Wu et al. |
| 2005/0017188 A1 | 1/2005 | Yagi |
| 2008/0078939 A1 | 4/2008 | Hennessy |
| 2009/0065703 A1 * | 3/2009 | Jadrich ............... G01T 1/2928 250/370.11 |
| 2009/0122959 A1 | 5/2009 | Jadrich et al. |
| 2010/0128850 A1 | 5/2010 | Konkle |
| 2010/0264572 A1 | 10/2010 | Konkle |

(Continued)

FOREIGN PATENT DOCUMENTS

| | | | |
|---|---|---|---|
| EP | 0250114 A1 | 12/1987 | |
| GB | 917317 A * | 2/1963 | ......... B21D 51/2646 |

(Continued)

OTHER PUBLICATIONS

EP Patent Application No. 18189150.8 Extended European Search Report dated Jan. 7, 2019, 10 pages.

*Primary Examiner* — Mark R Gaworecki

(57) ABSTRACT

An enclosure for a radiographic device includes a bottom panel, a plurality of sidewalls integrally formed with the bottom panel, whereby the plurality of sidewalls and the bottom panel define a unitary body, and a top panel joined to the plurality of sidewalls and defining an internal space therebetween for housing a radiographic device.

17 Claims, 5 Drawing Sheets

(56) References Cited

U.S. PATENT DOCUMENTS

| | | |
|---|---|---|
| 2011/0133096 A1 | 6/2011 | Konkle et al. |
| 2014/0009047 A1 | 1/2014 | Yanagisawa |
| 2014/0009048 A1 | 1/2014 | Yanagisawa |
| 2014/0270092 A1 | 9/2014 | Ogura et al. |
| 2015/0253441 A1 | 9/2015 | Horiuchi et al. |
| 2015/0276944 A1 | 10/2015 | Enomoto et al. |
| 2015/0327823 A1 | 11/2015 | Nariyuki |
| 2015/0366524 A1* | 12/2015 | Suzuki ................ A61B 6/4283 378/189 |
| 2016/0081638 A1 | 3/2016 | Ogura et al. |
| 2016/0081639 A1 | 3/2016 | Bettouyashiki et al. |
| 2016/0081649 A1 | 3/2016 | Enomoto et al. |
| 2016/0331334 A1 | 11/2016 | Imamura et al. |
| 2016/0339537 A1 | 11/2016 | Wu et al. |

FOREIGN PATENT DOCUMENTS

| | | |
|---|---|---|
| WO | 2016168151 A1 | 10/2016 |
| WO | 2018093908 A1 | 5/2018 |

* cited by examiner

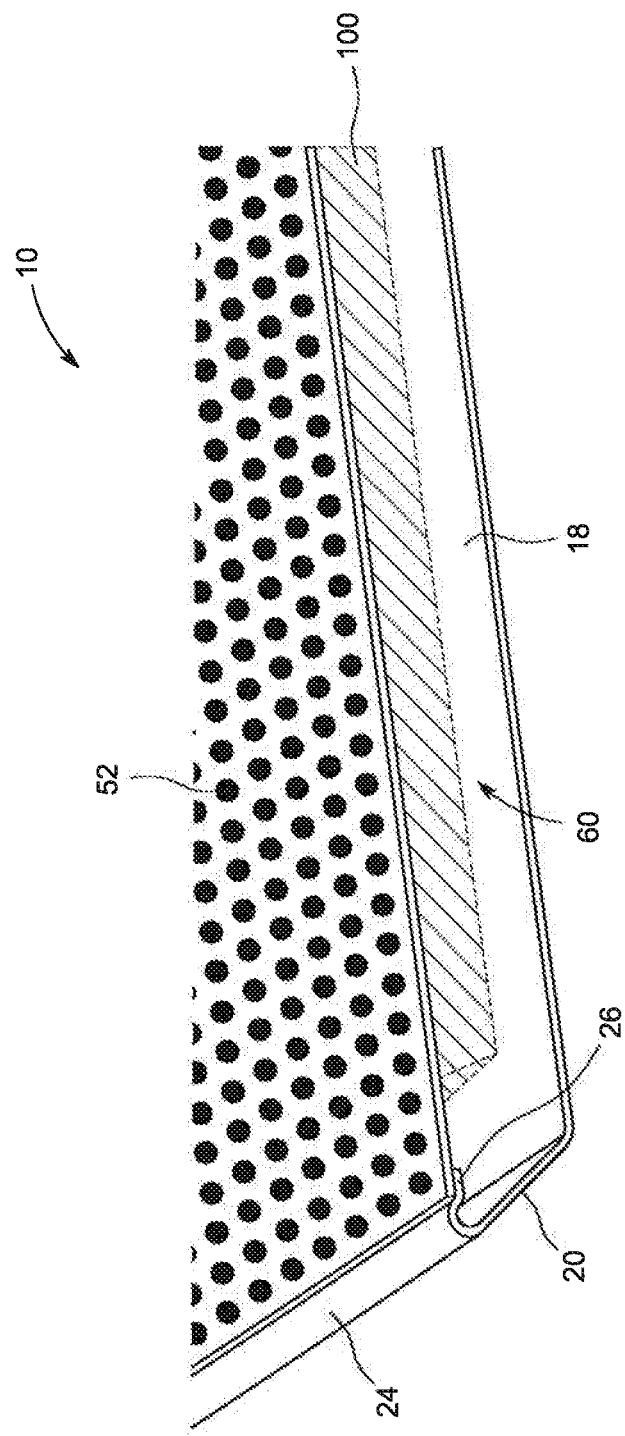

APPARATUS FOR A RADIOGRAPHIC DEVICE

BACKGROUND

Technical Field

Embodiments of the invention relate generally to imaging systems, and more particularly, to a protective enclosure for a radiographic device such as an x-ray detector.

Discussion of Art

Imaging systems are utilized for various applications in both medical and non-medical fields. For example, medical imaging systems include general radiological, mammography, x-ray C-arm, tomosynthesis, and computed tomography (CT) imaging systems. These various imaging systems, with their different respective topologies, are used to create images or views of a patient for clinical diagnosis based on the attenuation of radiation (e.g., x-rays) passing through the patient. Alternatively, imaging systems may also be utilized in non-medical applications, such as in industrial quality control or in security screening of passenger luggage, packages, and/or cargo. In such applications, acquired data and/or generated images representing volumes or parts of volumes (e.g., slices) may be used to detect objects, shapes or irregularities which are otherwise hidden from visual inspection and which are of interest to the screener.

Typically, x-ray imaging systems, both medical and non-medical, utilize an x-ray tube to generate the x-rays used in the imaging process. The generated x-rays pass through the imaged object where they are absorbed or attenuated based on the internal structure and composition of the object, creating a matrix or profile of x-ray beams of different strengths. The attenuated x-rays impinge upon an x-ray detector designed to convert the incident x-ray energy into a form usable in image reconstruction. Thus the x-ray profile of attenuated x-rays is sensed and recorded by the x-ray detector. Typically, x-ray detectors are based on film-screen, computed radiography (CR) or digital radiography (DR) technologies. In film-screen detectors, the x-ray image is generated through the chemical development of the photo-sensitive film after x-ray exposure. In CR detectors, a storage phosphor imaging plate captures the radiographic image. The plate is then transferred to a laser image reader to "release" the latent image from the phosphor and create a digitized image. In DR detectors, a scintillating layer absorbs x-rays and subsequently generates light, which is then detected by a two-dimensional (2D) flat panel array of silicon photo-detectors. Absorption of light in the silicon photo-detectors creates electrical charge. A control system electronically reads out the electrical charge stored in the x-ray detector and uses it to generate a viewable digitized x-ray image.

Digital x-ray detector manufacturers typically fabricate the 2D flat panel array of silicon photo-detectors on a glass substrate (imaging panel). Since the imaging panel is fragile, it must therefore be mechanically supported, by some type of panel supports, during use. The panel support also provides stiffness to the overall detector package. Additionally, an external housing or enclosure may be provided to protect the imaging panel. A portion of this external enclosure is generally comprised of a material with low x-ray attenuation characteristics to allow incident x-ray radiation to readily reach the imaging panel.

Typically, the panel supports and the external protective enclosures are composed of stiff machined metal, such as magnesium, so as to provide a high degree of mechanical protection to the flat panel substrate and associated read-out electronic components located within the external housing. Further, the currently available x-ray detectors are based on multi-piece metallic external enclosure assemblies having many weak mechanical seams and screw fasteners both of which are prone to mechanical failure if the detector is dropped or impacted with a rigid object.

Thus, the conventional construction of x-ray detectors, being manufactured from stiff materials, results in a relatively heavy and thick x-ray detector that is prone to mechanical failure upon dropping the detector onto a hard surface (i.e. case can dent or break apart). This is particularly problematic for portable x-ray detector designs that should be ideally lightweight while withstanding multiple accidental impact loads. However, the relatively thick and heavy panel support and external enclosure has typically been required to protect the sensitive and fragile imaging components and the readout electronics as these portable detectors are typically used in environments where they can be dropped, impacted with a rigid object, or subjected to a patient load, e.g., placed directly beneath a patient being imaged.

It is therefore desirable to provide an outer case or enclosure for an x-ray detector that is cost efficient and impact resistant, and which is easier to manufacture and assemble than existing enclosures.

BRIEF DESCRIPTION

In an embodiment, an enclosure for a radiographic device is provided. The enclosure includes a bottom panel, a plurality of sidewalls integrally formed with the bottom panel, whereby the plurality of sidewalls and the bottom panel define a unitary body, and a top panel joined to the plurality of sidewalls and defining an internal space therebetween for housing a radiographic device.

In another embodiment, a method of manufacturing an enclosure for a radiographic device is provided. The method includes the steps of bending a sheet of material to form a plurality of sidewalls and a bottom panel integrally formed with the plurality of sidewalls, inserting a corner member into cutouts between each sidewall, and affixing a top panel to the sidewalls and the corner members to define an interior space between the top panel, bottom panel and plurality of sidewalls for receiving a radiographic device.

In yet another embodiment, a detector for an imaging system is provided. The detector includes a bottom panel, a plurality of sidewalls integrally formed with the bottom panel, whereby the plurality of sidewalls and the bottom panel define a unitary body formed from a single sheet of material, a top panel joined to the plurality of sidewalls and defining an internal space therebetween, and a radiographic detector housed within the internal space.

DRAWINGS

The present invention will be better understood from reading the following description of non-limiting embodiments, with reference to the attached drawings, wherein below:

FIG. 5 is a cross-sectional, perspective view of a portion of the enclosure of FIG. 1, shown with a top panel in place and housing a detector of an imaging system.

DETAILED DESCRIPTION

Figure 1:
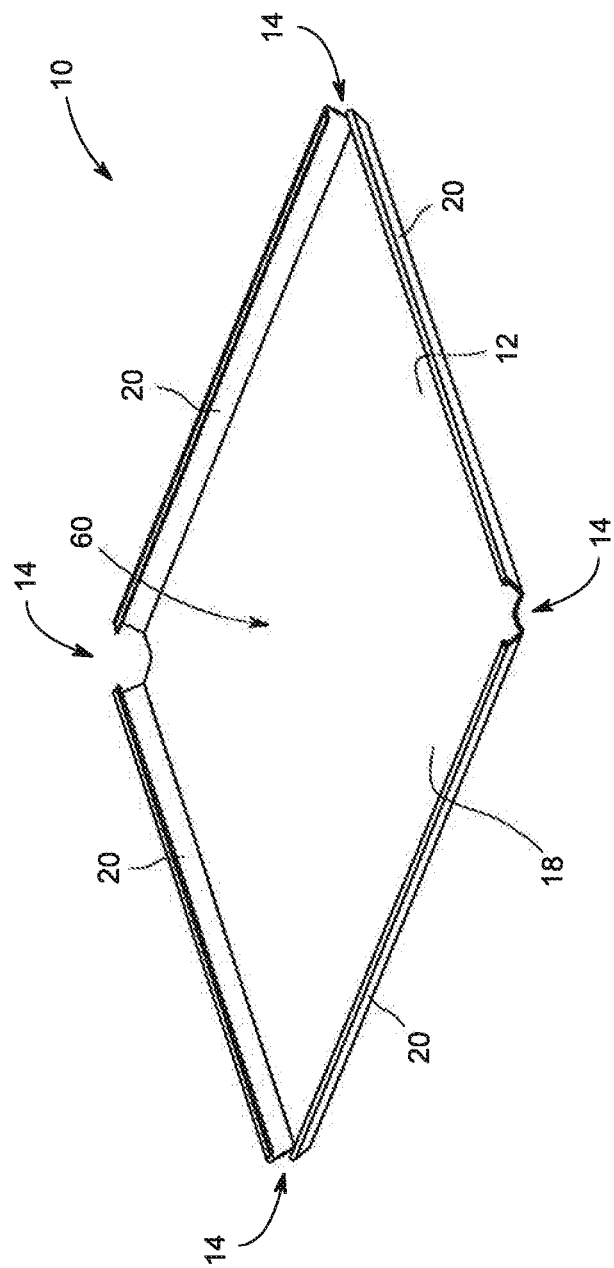
FIG. 1 is a perspective view of enclosure for an x-ray detector, according to an embodiment of the invention.

Reference will be made below in detail to exemplary embodiments of the invention, examples of which are illustrated in the accompanying drawings. Wherever possible, the same reference characters used throughout the drawings refer to the same or like parts, without duplicative description.

Embodiments of the invention are directed to an enclosure for an x-ray detector used in a variety of imaging systems, such as for medical imaging, industrial imaging, and baggage or package screening. Though the invention provides examples in a medical imaging context, one of ordinary skill in the art will readily comprehend that the application of these detectors and enclosure in other contexts, such as for industrial imaging, security screening, and/or baggage or package inspection, is well within the scope of the invention. While the invention is described with respect to a digital flat panel, solid-state, direct detection x-ray detector for use with an x-ray imaging system, the invention is equivalently applicable with other types of x-ray detectors including indirect detection digital detectors. Additionally, the invention may be used with stationary or fixed room x-ray imaging systems, as well as portable or mobile systems. Further, the invention described herein makes reference to an imaging "subject" as well as an imaging "object". These terms are not mutually exclusive and, as such, use of the terms is interchangeable and is not intended to limit the scope of the appending claims. As used herein, the terms "substantially," "generally," and "about" indicate conditions within reasonably achievable manufacturing and assembly tolerances, relative to ideal desired conditions suitable for achieving the functional purpose of a component or assembly.

Referring to FIG. 1, an enclosure 10 for a radiographic device such as, for example, an x-ray detector, is illustrated. As show therein, the enclosure 10 is formed from a rectangular sheet 12 of material having relief cutouts 14 at the corners thereof. The relief cutouts 14 may be formed or notched prior to bending the sheet, as discussed hereinafter. The sheet 12 is bent upwards intermediate the respective relief cutouts 14 to form an open-top enclosure having a bottom panel 18 and sidewalls 20. The bottom panel 18 and sidewalls 20 define a unitary body, also referred to herein as a unibody. As used herein, unitary body or unibody means a single piece construction without any mechanical joints, connections or the like using welding, adhesives, fasteners, etc. In an embodiment, the sheet 12 of material is a thin sheet of material such as, for example, sheet metal having a thickness in the range of about 0.5 millimeters to about 1.5 millimeters. Other materials known in the art including, for example, light weight alloys such as magnesium-lithium alloys having a stiffness to weight ratio that is similar to carbon fiber laminates, may also be utilized without departing from the broader aspects of the invention.

Figure 2:
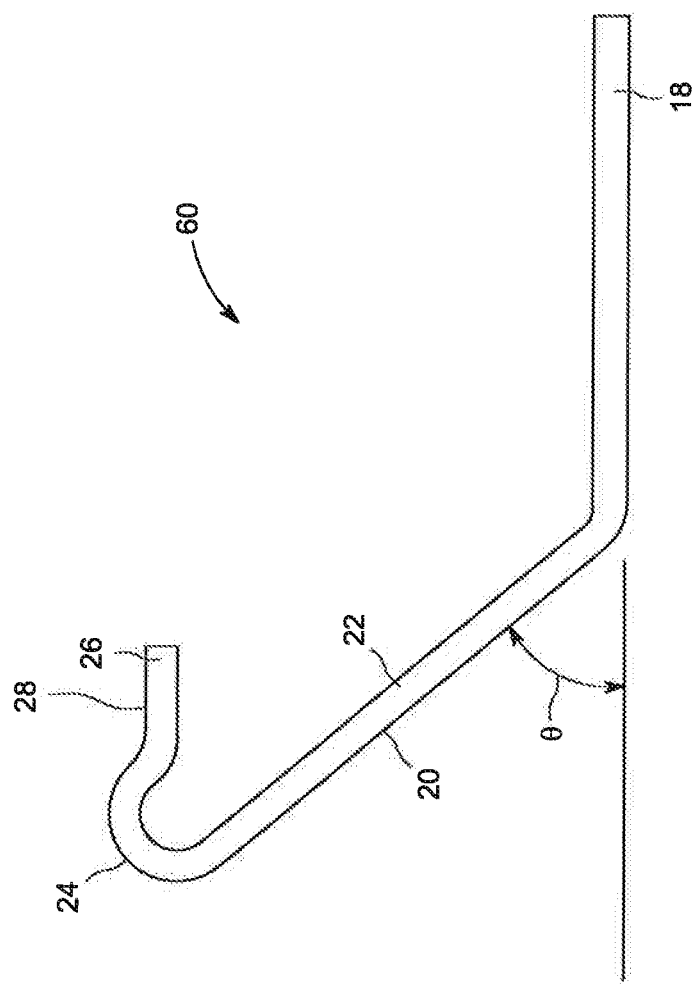
FIG. 2 is a cross-sectional, elevational view of the enclosure of FIG. 1.

Referring now to FIG. 2, a cross-sectional illustration of the enclosure 10, and the bottom panel 18 and one sidewall 20 thereof, is shown. The bottom panel 18 is substantially planar and is bent upwardly between the cutouts 14 to form the sidewall 20. As illustrated in FIG. 2, the sheet 12 of material is bent so that the resulting sidewall forms an angle, θ, with a horizontal surface upon which the enclosure is placed 10, the purposes of which will be described hereinafter. In an embodiment, the angle, θ, is greater than 0° and less than 90°. In an embodiment, the angle, θ, is between about 10° and about 80°. In an embodiment, the angle, θ, is between about 20° and about 70°. In an embodiment, the angle, θ, is between about 30° and about 60°. In an embodiment, the angle, θ, is between about 40° and about 50°. In an embodiment, the angle, θ, may be approximately 45°.

With further reference to FIG. 2, the sidewall 20 includes a first upturned portion 22, which extends from the bottom panel 18 and forms an angle, θ, with a horizontal surface upon which the enclosure is placed 10. The end of the first upturned portion 22 is turned towards the interior of the enclosure 10 and rounded back towards the bottom panel 18, forming a return portion or nose 24. The return portion 24 is extended to form a projection 26 that extends towards the interior of the enclosure 10 and is oriented substantially parallel to the bottom panel 18. As shown therein, and as discussed hereinafter, a top surface of the projection 26 defines a flange 28 for receiving a top panel of the enclosure 10, as discussed in detail hereinafter.

Figure 3:
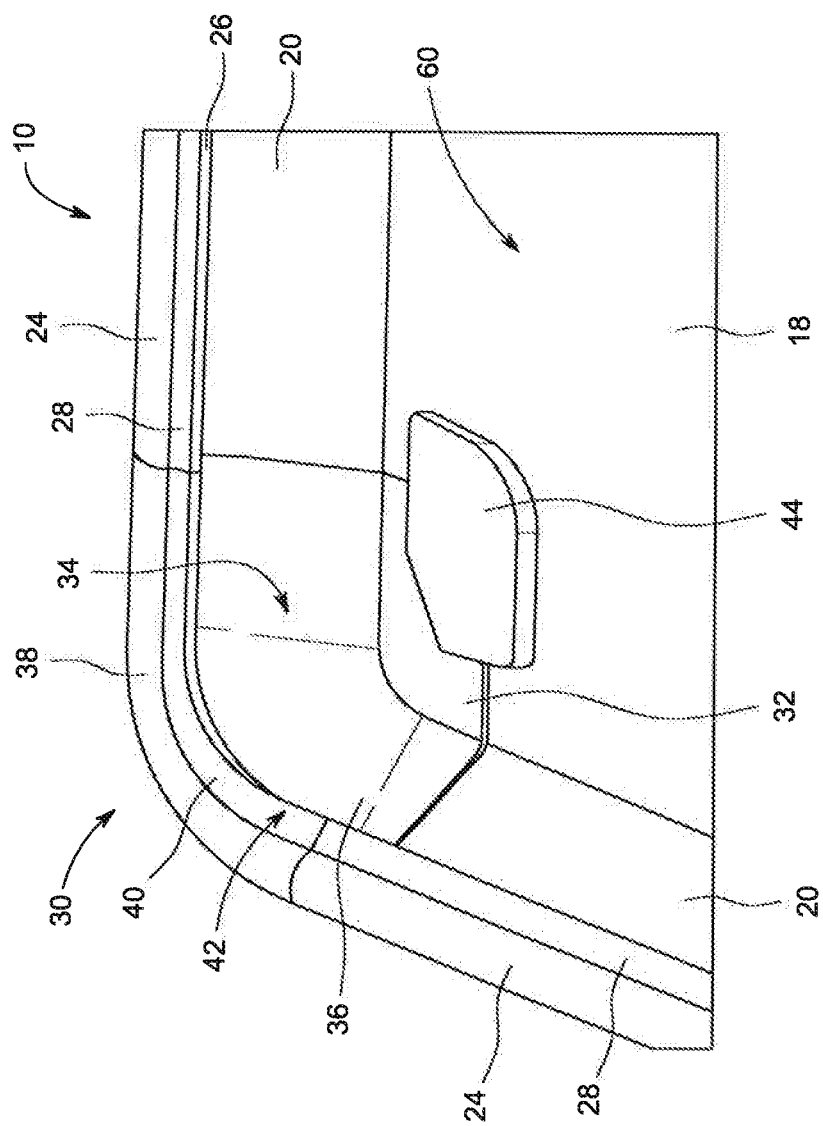
FIG. 3 is an enlarged, perspective view of a corner portion of the enclosure of FIG. 1, shown with a corner member installed.

Turning now to FIG. 3, the enclosure 10 further includes corner members 30 received in each of the cutouts 14 after the sidewalls 20 are bent to shape. As illustrated in FIG. 3, the corner members 30 have a shape that corresponds to the shape of the cutouts 14, and a cross-section that substantially corresponds to the cross-section of the sidewalls 20. For example, the corner members 30 may include a generally planar bottom portion 32 and a sidewall portion 34. The sidewall portion 34 includes a first upturned portion 36 which extends from the bottom portion 32 at an angle, a return portion or nose 38 which is rounded back towards the bottom portion 32, and an inward projection portion 40 having an upward-facing surface that defines a flange 42. In this respect, the sidewall portion 34 has a height that is substantially coextensive with the sidewalls 20. As illustrated in FIG. 3, the corner members 30 are inserted into the cutouts 14 so that the flange 28 of the sidewalls 20 and the flange 42 of the corner members 30 define a substantially continuous supporting surface for a top panel of the enclosure 10.

In an embodiment, the sidewall portion 34 and/or the bottom planar portion 32 of the corner members 30 may be dimensionally larger than the corresponding cutouts 14 so that the corner members 30 at least partially overlap the sidewalls 20 or bottom panel 18. As illustrated in FIG. 3, for example, the bottom planar portion 32 may include an overhanging portion 44 that lies on top or beneath the bottom panel 18.

Figure 4:
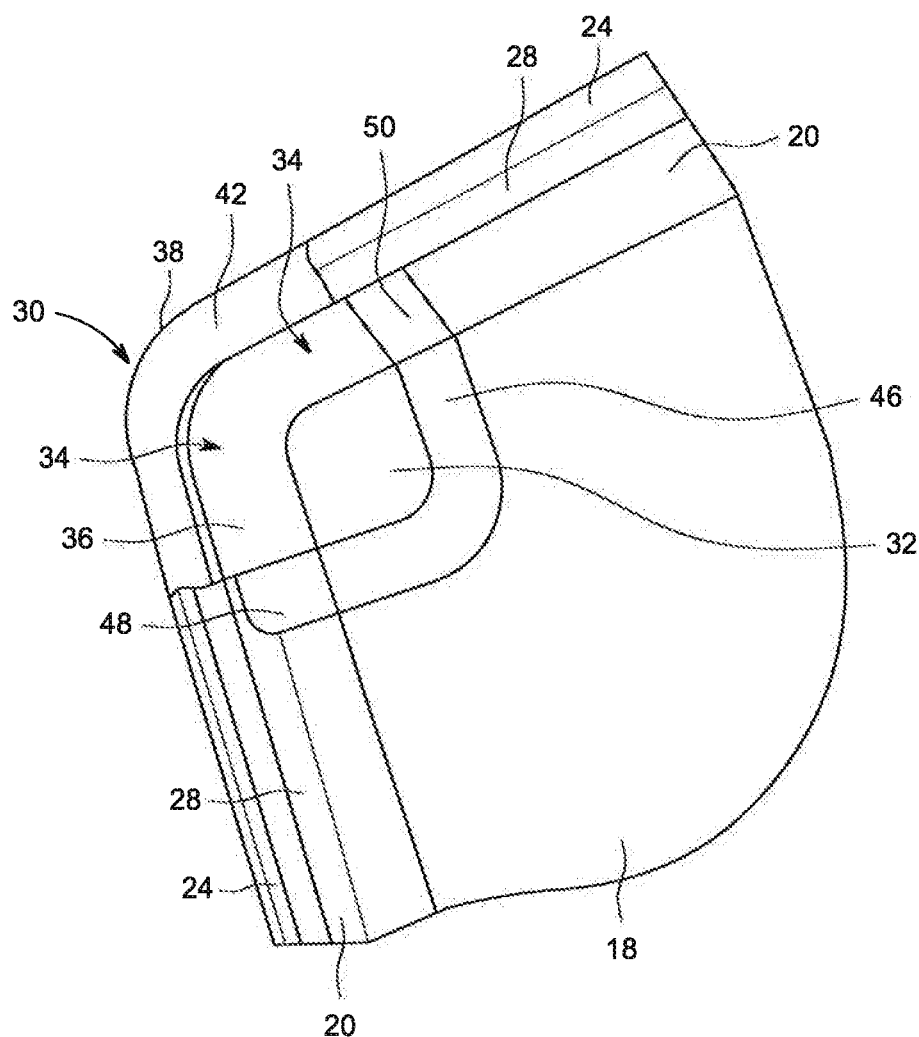
FIG. 4 is another enlarged, preserve view of a corner portion of the enclosure of FIG. 1, shown with a corner member according to another embodiment of the invention.

Turning now to FIG. 4, in an embodiment, the corner members 30 may having an overhanging bottom portion 46 formed as part of the bottom portion 32 of the corner members 30, as well as overhanging sidewall portions 46, 48 formed as part of the upturned portion 36 of sidewall portion 34 of the corner members 30. This configuration provides for overlap at both the sidewalls and the bottom of the corner members 30 with respect to the bottom panel 18 and sidewalls 20.

In an embodiment, the overlap between the corner members 30 and the bottom panel 18 and/or sidewalls 20 may be between about 0 millimeters and about 20 millimeters. In an embodiment, the overlap may be between about 5 millimeters and about 15 millimeters. In an embodiment, the overlap may be approximately 10 millimeters. In an embodiment, the overlap may be greater than about 10 millimeters. As will be readily appreciated, a greater surface area for the overlap results in a more robust connection. It is contemplated that the corner members 30 may likewise be formed from sheet metal, although other materials such as plastic or other metals may also be utilized without departing from the broader aspects of the invention. In either implementation, the corner members 30 may be joined to the sidewalls 20 and/or bottom panel 18 using an epoxy or adhesive in the area of the overlap. In certain embodiments, welding may be utilized to join the corner members. In yet other embodiments, the joining may be made using an embedment of a liquid urethane material, a lamination or one or more stakes. Utilizing adhesives, epoxies or welding creates a substantially fluid-tight connection between the corner members 30 and the bottom panel 18 and sidewalls 20, helping to prevent the leakage of fluid into the enclosure 10. In yet other embodiments, rivets, screws or other mechanical fasteners may be utilized to fixedly secure the corner members 30 to the bottom panel 18 and sidewalls 20.

Turning finally to FIG. 5, the enclosure 10 further includes a top panel 52. In an embodiment, the top panel 52 is formed from a material that is x-ray translucent and is opaque to light, such as, for example, carbon fiber reinforced polymer. As shown therein, the top panel 52 is dimensioned so as to be received by an inner periphery of the enclosure defined by the nose 24. The top panel 52 is received and supported by the substantially continuous supporting surface defined by the flanges 28, 42 of the sidewalls 20 and corner members 30, and defines, in concert with the sidewalls 20, corner members 30 and bottom panel 18, and internal space 60. In an embodiment, the top panel 52 is fixedly secured to the flanges 28, 42 by a bead of adhesive or by welding, which likewise creates a fluid-tight seal preventing the incursion of fluid into the enclosure 10. In an embodiment, the top panel 52 may be secured to the flanges 28, 42 using mechanical fasteners such as screws or rivets. In either implementation, the thickness of the top panel and the configuration of the nose and flanges of the sidewalls 20 and corner member 30 is such that the top panel 52 is positioned (or recessed) lower than an uppermost portion of the nose 24. Accordingly, in the event of a drop or other impact, the rounded nose portion 24, 28 will bear the force of the impact, rather than the top panel 52.

With further reference to FIG. 5, an x-ray detector 100 and associated electronics may be attached to the underside of the top panel 52, although other mounting configurations are likewise possible. The x-ray detector 100 may be of any type known in the art, including, for example, non-glass substrate type x-ray detectors.

The enclosure 10 for an x-ray detector of the invention thus consists of a sheet metal unibody (defining the bottom and sides of the enclosure), a plurality of universal corner members, and a top panel (thus only three distinct parts). Where the enclosure is rectangular in shape, the enclosure thus includes a sheet metal unibody, four universal corner members, and a top panel. Utilizing a sheet metal unibody that defines the bottom and sidewalls of the enclosure simplifies manufacturing as compared to existing detector enclosures which typically use separate pieces for the top, bottom, sides and corners. In particular, the enclosure 10 of the invention enables the reduction of distinct components from separate edge pieces to just separate corner members, which reduces the amount of bonding and machining required. That is, utilizing a unibody for the bottom and sidewalls, formed form bent sheet metal, enables a reduction in both parts and the number of bonds required, without necessitating a corresponding increase in machining and bonding costs. Moreover, because the corner members are 'universal,' meaning that they are substantially identical in shape and can be used at any of the corners of the enclosure 10, the corner members may be manufactured at higher volume such as by machining, molding or casting.

In addition to providing an ease and cost of manufacture heretofore not seen in the art, the enclosure 10 of the invention provides an enhanced level of protection for the internal detector as compared to existing devices. In particular, the recess created by the bends in the sidewalls (and in particular, the presence of the nose) allow the top panel to be slightly inset, allowing the nose of the sidewalls to absorb impacts and preventing the top panel, itself, from directly contacting the floor or other surface during a drop or impact. Moreover, the sheet metal construction of the unibody actually allows the enclosure 10 itself to absorb impact forces. That is, the sheet metal can dent or deform in response to an impact, absorbing the forces of impact rather than transmitting them to the enclosed detector 100. This is particularly useful where flexible, i.e., non-glass substrate, x-ray detectors are utilized. In particular, non-glass detectors or imagers tend to be more flexible than their glass substrate counterparts, meaning that absolute rigidity in the protective case is no longer necessary. In certain embodiments, forming the corner members from a material other than sheet metal, e.g., plastic, may provide for even greater drop strength.

As alluded to above, the overlap of the corner members 30 with the bottom panel 18 and sidewalls 20 of the unibody, and the use of an epoxy or adhesive to join the corner members 30 and top panel 52 to the unibody, results in a substantially fluid-tight enclosure. The angled sidewalls 20 of the unibody (i.e., at an angle of less than 90 degrees with respect to horizontal) provides for easier gripping and handling of the enclosure, particularly when lifting from a surface.

In an embodiment, an enclosure for a radiographic device is provided. The enclosure includes a bottom panel, a plurality of sidewalls integrally formed with the bottom panel, whereby the plurality of sidewalls and the bottom panel define a unitary body, and a top panel joined to the plurality of sidewalls and defining an internal space therebetween for housing a radiographic device. In an embodiment, the enclosure includes a plurality of cutouts separating each sidewall of the plurality of sidewalls, and a corner member positioned within each cutout and affixed to the unitary body. In an embodiment, each corner member is substantially identical. In an embodiment, each corner member is affixed to the unitary body with one of an adhesive and an epoxy. In an embodiment, the unitary body is formed from sheet metal. In an embodiment, the top panel is formed from a carbon fiber reinforced polymer. In an embodiment, the plurality of sidewalls each include a first upturned portion that extends upwardly from the bottom panel, a return portion extending from the first upturned portion back towards the bottom panel and defining a rounded nose, and an inward projection extending from the return portion generally parallel to the bottom panel and defining a flange for supporting the top panel. In an embodiment, the first upturned portion forms an angle of less than 90 degrees with a horizontal surface supporting the enclosure. In an embodiment, the flange is spaced a vertical distance below a top of the rounded nose such that the top panel is inset with respect to the rounded nose. In an embodiment, the enclosure may further include a non-glass x-ray detector received within the interior space. In an embodiment, the enclosure is substantially fluid-tight. In an embodiment, the enclosure is substantially rectangular in shape, and the plurality of corner members is four corner members.

In another embodiment, a method of manufacturing an enclosure for a radiographic device is provided. The method includes the steps of bending a sheet of material to form a plurality of sidewalls and a bottom panel integrally formed with the plurality of sidewalls, inserting a corner member into cutouts between each sidewall, and affixing a top panel to the sidewalls and the corner members to define an interior space between the top panel, bottom panel and plurality of sidewalls for receiving a radiographic device. In an embodiment, the method may further include the step of, prior to bending the sheet of material, notching corners of the sheet of material to form the cutouts. In an embodiment, the method may also include creating an overlap between the corner members and at least one of the bottom panel and the sidewalls, and adhering the corner members and the at least one of the bottom panel and the sidewalls in the area of the overlap. In an embodiment, the method may include bending the sheet of material to provide each sidewall with a first upturned portion that extends upwardly from the bottom panel, a return portion that extends from the first upturned portion back towards the bottom panel and defines a rounded nose, and an inward projection that extends from the return portion generally parallel to the bottom panel, wherein the inward projection includes an upper surface that defines a flange for supporting the top panel. In an embodiment, the first upturned portion forms an angle of less than 90 degrees with a horizontal surface supporting the enclosure. In an embodiment, the flange is spaced a vertical distance below a top of the rounded nose such that the top panel is inset with respect to the rounded nose.

In yet another embodiment, a detector for an imaging system is provided. The detector includes a bottom panel, a plurality of sidewalls integrally formed with the bottom panel, whereby the plurality of sidewalls and the bottom panel define a unitary body formed from a single sheet of material, a top panel joined to the plurality of sidewalls and defining an internal space therebetween, and a radiographic detector housed within the internal space. In an embodiment, the detector may also include a plurality of cutouts separating each sidewall of the plurality of sidewalls, and a corner member positioned within each cutout and affixed to the unitary body. Each sidewall may include a first upturned portion that extends upwardly from the bottom panel, a return portion extending from the first upturned portion back towards the bottom panel and defining a rounded nose, and an inward projection extending from the return portion generally parallel to the bottom panel and defining a flange for supporting the top panel.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property.

This written description uses examples to disclose several embodiments of the invention, including the best mode, and also to enable one of ordinary skill in the art to practice the embodiments of invention, including making and using any devices or systems and performing any incorporated methods. The patentable scope of the invention is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An enclosure for a radiographic device, comprising:
a bottom panel;
a plurality of sidewalls integrally formed with the bottom panel, whereby the plurality of sidewalls and the bottom panel define a unitary body; and
a top panel joined to the plurality of sidewalls opposite the bottom panel and defining an internal space therebetween for housing a radiographic device;
wherein the plurality of sidewalls each include a first upturned portion that extends upwardly from the bottom panel, a return portion extending from the first upturned portion back towards the bottom panel and defining a rounded nose, and an inward projection extending from the return portion generally parallel to the bottom panel and defining a flange for supporting the top panel.

2. The enclosure of claim 1, further comprising:
a plurality of cutouts separating each sidewall of the plurality of sidewalls; and
a plurality of corner members, each of the corner member positioned within a corresponding cutout of the plurality of cutouts and affixed to the unitary body.

3. The enclosure of claim 2, wherein:
each corner member is substantially identical.

4. The enclosure of claim 3, wherein:
each corner member is joined to the unitary body with one of an adhesive, an epoxy, a braze, a weld, an embedment of a liquid urethane material, a lamination and stakes.

5. The enclosure of claim 1, wherein:
the unitary body is formed from sheet metal.

6. The enclosure of claim 5, wherein:
the top panel is formed from a carbon fiber reinforced polymer.

7. The enclosure of claim 1, wherein:
the first upturned portion forms an angle of less than 90 degrees with a horizontal surface supporting the enclosure.

8. The enclosure of claim 1, wherein:
the flange is spaced a vertical distance below a top of the rounded nose such that the top panel is inset with respect to the rounded nose.

9. The enclosure of claim 1, further comprising:
a non-glass x-ray detector received within the interior space.

10. The enclosure of claim 1, wherein:
the enclosure is substantially fluid-tight.

11. The enclosure of claim 1, wherein:
the enclosure is substantially rectangular in shape; and
the plurality of corner members is four corner members.

12. A method of manufacturing an enclosure for a radiographic device, comprising the steps of:
- bending a sheet of material to form a plurality of sidewalls and a bottom panel integrally formed with the plurality of sidewalls;
- inserting a corner member into cutouts between each sidewall;
- affixing a top panel to the sidewalls and the corner members to define an interior space between the top panel, bottom panel and plurality of sidewalls for receiving a radiographic device;
- bending the sheet of material to provide each sidewall with a first upturned portion that extends upwardly from the bottom panel, a return portion that extends from the first upturned portion back towards the bottom panel and defines a rounded nose, and an inward projection that extends from the return portion generally parallel to the bottom panel;
- wherein the inward projection includes an upper surface that defines a flange for supporting the top panel.

13. The method according to claim 12, further comprising the step of:
- prior to bending the sheet of material, notching corners of the sheet of material to form the cutouts.

14. The method according to claim 13, further comprising the step of:
- creating an overlap between the corner members and at least one of the bottom panel and the sidewalls; and
- adhering the corner members and the at least one of the bottom panel and the sidewalls in the area of the overlap.

15. The method according to claim 12, wherein:
the first upturned portion forms an angle of less than 90 degrees with a horizontal surface supporting the enclosure.

16. The method according to claim 12, wherein:
the flange is spaced a vertical distance below a top of the rounded nose such that the top panel is inset with respect to the rounded nose.

17. A detector for an imaging system, comprising:
- a bottom panel;
- a plurality of sidewalls integrally formed with the bottom panel, whereby the plurality of sidewalls and the bottom panel define a unitary body formed from a single sheet of material;
- a top panel joined to the plurality of sidewalls opposite the bottom panel and defining an internal space therebetween;
- a radiographic detector housed within the internal space;
- a plurality of cutouts separating each sidewall of the plurality of sidewalls; and
- a corner member positioned within each cutout and affixed to the unitary body;
- wherein each sidewall includes a first upturned portion that extends upwardly from the bottom panel, a return portion extending from the first upturned portion back towards the bottom panel and defining a rounded nose, and an inward projection extending from the return portion generally parallel to the bottom panel and defining a flange for supporting the top panel.

\* \* \* \* \*